US005962726A

United States Patent [19]
Kwetkat et al.

[11] Patent Number: 5,962,726
[45] Date of Patent: Oct. 5, 1999

[54] AMPHIPHILIC COMPOUNDS WITH SEVERAL HYDROPHILIC AND HYDROPHOBIC GROUPS BASED ON ALKOXYLATED AMINES AND/OR AMIDES AND DI-, OLIGO- OR POLYCARBOXYLIC ACIDS

[75] Inventors: Klaus Kwetkat, Lünen; Herbert Koch, Dorsten; Wulf Ruback, Dülmen, all of Germany

[73] Assignee: Hüls Aktiengesellschaft, Marl, Germany

[21] Appl. No.: 08/973,862

[22] PCT Filed: May 24, 1996

[86] PCT No.: PCT/EP96/00224

§ 371 Date: Jan. 29, 1998

§ 102(e) Date: Jan. 29, 1998

[87] PCT Pub. No.: WO97/02234

PCT Pub. Date: Jan. 23, 1997

[30] Foreign Application Priority Data

Jul. 3, 1995 [DE] Germany .......................... 195 24 127

[51] Int. Cl.$^6$ ...................... C07C 229/22; C07C 315/06; B01D 17/04
[52] U.S. Cl. .......................... 560/171; 560/151; 562/556; 562/564; 252/341; 252/344
[58] Field of Search .................................. 252/341, 344; 562/556, 564; 560/151, 171

[56] References Cited

U.S. PATENT DOCUMENTS 5,160,450  11/1992  Okahara et al. .
5,385,674   1/1995  Kupfer et al. .......................... 210/708

FOREIGN PATENT DOCUMENTS

| 0035263 | 9/1981 | European Pat. Off. . |
| 3032216 | 4/1982 | Germany . |
| 4217985 | 12/1993 | Germany . |
| 04124165 | 12/1990 | Japan . |
| WO A 8603741 | 7/1986 | WIPO . |

OTHER PUBLICATIONS

Chemical Abstract, vol. 106, No. 22, Jun. 1, (1987), abstract No. 178503, Higuchi, Hisao, et al: "Dispersing agent for nonaqueous solids".

Chemical Abstract, vol. 83, No. 14, Oct. 6, (1975), abstract No. 116823, Sugita, Yoshio, et al: "Pilling–resistant acrylic fibers".

Database Crossfire, siehe BRN 1716007 & Pharm. Bull., vol. 2, (1954), pp. 220,224.

American Chemical Society, vol. 7, No. 6, (1991), pp. 1072–1075, "Alkanediyl–α,ω bis(dimethylalkylammonium bromide) Surfactants. 1. Effect of the Spacer Chain Length on the Critical Micelle Concentration and Micelle Ionization Degree", R. Zana, et al.

American Chemical Society, vol. 9, (1993), pp. 1465–1467, "Alkanediyl–α,ω–bis (dimethylalkylammonium bromide) Surfactants. 3. Behavior at the Air–Water Interface", E. Alami, et al.

Nature, vol. 362, Mar. 18, (1993), pp. 228–230, "Dependence of aggregate morphology on structure of dimeric surfactants", R. Zana, et al.

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

The invention relates to amphiphilic compounds of the general formula I

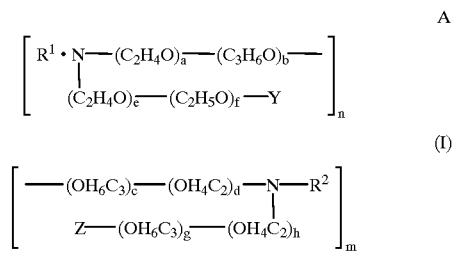

with at least two hydrophilic and at least two hydrophobic groups based on alkoxylated amines and/or alkoxylated fatty acid amides and di-, oligo- or polycarboxylic acids (spacer A). Y and Z are hydrogen or functional groups. The amphiphilic compounds according to this invention are usually surface-active and are suitable as emulsifiers, demulsifiers, detergents, dispersants and hydrotropes in industry and domestically, for example in the areas of metal processing, ore production, surface treatment, washing and cleaning hard surfaces, such as, for example, the manual cleaning of crockery, washing and cleaning skin and hair, cosmetics, medicine and food processing and preparation.

9 Claims, No Drawings

AMPHIPHILIC COMPOUNDS WITH SEVERAL HYDROPHILIC AND HYDROPHOBIC GROUPS BASED ON ALKOXYLATED AMINES AND/OR AMIDES AND DI-, OLIGO- OR POLYCARBOXYLIC ACIDS

The invention relates to amphiphilic compounds with a plurality of hydrophilic and hydrophobic groups based on amines and/or amides and di-, oligo- or polycarboxylic acids.

A wide variety of anionic, cationic, nonionic and zwitterionic compounds are known as amphiphilic substances. By far the majority of these substances consist of a hydrophilic head group and at least one hydrophobic moiety.

With the amphiphilic substances there is a need, for ecological reasons, for example concerning the reduction in the cost of packaging and transport, to achieve an increasingly great effect per mass of substance employed. Since optimization by mixing amphiphilic substances produces only very limited advances, novel amphiphilic substances with greater efficiency are required. It is therefore necessary in particular to find substances with lower critical micelle concentrations and/or lower surface and interfacial tensions in order to be able to reduce markedly the amounts of active substance used. In addition, they must be easily obtainable, most favourably from readily available starting substances.

Initial approaches to a solution in this direction by doubling one part of the structure (hydrophilic head group, hydrophobic group) have already been disclosed. Thus, cationic surface-active compounds can be obtained by adding long-chain alkyl halides onto permethylated alkylenediamines [R. Zana, M. Benrraou, R. Rueff, Langmuir, 7 (1991) 1072; R. Zana, Y. Talmon, Nature, 362 (1993) 228; E. Alami, G. Beinert, P. Marie, R. Zana, Langmuir, 9 (1993) 1465].

Anionic surface-active compounds with at least two hydrophilic and at least two hydrophobic groups have to date been prepared on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues, so that these compounds are no longer in accord with the times from the ecotoxicological and economic viewpoints.

The object therefore was to find amphiphilic compounds which have at least two hydrophilic and at least two hydrophobic groups, the amphiphilic compounds having a very high efficiency relative to the amount used, and which furthermore can be prepared from raw materials which are readily available industrially and without large amounts of unwanted byproducts being formed.

The object is achieved according to the invention by amphiphilic di- or oligoesters whose basic skeletons can be prepared from di-, oligo- or polycarboxylic acids and alkoxylated fatty amines or fatty acid amides. The corresponding di- or oligoesters are nonionic surfactants which, however, can be reacted further to give anionic amphiphilic compounds, for which sulphation, carboxymethylation or conversion, for example, into isethionates, taurates or sulphosuccinates are suitable.

The invention therefore relates to amphiphilic compounds of the general formula I:

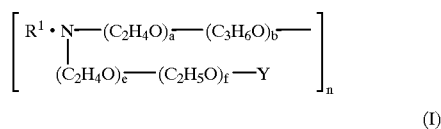
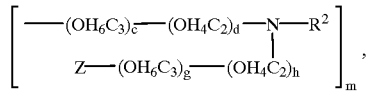

(I)

in which $R^1$ and $R^2$ are, independently of one another, an unbranched or branched, saturated or unsaturated hydrocarbon radical with 1 to 22, preferably 6 to 18, carbon atoms or an unbranched or branched, saturated or unsaturated acyl radical with 2 to 23, preferably 7 to 19, carbon atoms, A is a spacer and Y and Z are hydrogen or functional groups, and n and m are each, independently of one another, at least 1.

Specific substituents $R^1$ and $R^2$ which may be mentioned are the radicals methyl,;..ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl and their branched-chain isomers, and the corresponding singly, doubly or triply unsaturated radicals and the corresponding acyl compounds.

A is a straight-chain or branched, saturated or unsaturated, acyclic or cyclic, aliphatic or aromatic di-, oligo- or polycarboxylic acid.

a, b, c, d, e, f, g and h are, independently of one another, numbers from 0 to 15, where the total of a and b, c and d, e and f and g and h must in each case be at least 1, and where -the alkoxide units are incorporated randomly or blockwise in any desired sequence. Y and Z are, independently of one another, hydrogen or a functional radical, —CH$_2$COOM, —SO$_3$M, —C$_2$H$_4$SO$_3$M, —C(O)C$_2$H$_3$(SO$_3$M)COOM', —P(O) (OM)$_2$ with M, M'=alkali metal, ammonium, alkanolammonium or ½ alkaline earth metal.

The amphiphilic compounds according to the invention are usually distinguished by extremely low critical micelle concentrations (CMC) and very low surface and interfacial tensions (for example in the presence of paraffin), which must be ascribed to their special structure—at least two hydrophilic groups and at least two hydrophobic groups. Furthermore, most of them display a rather high hydrophilic suspension capacity which is about halfway between that of conventional surfactants and that of pentasodium tripolyphosphate. Some of these compounds are extremely rapid wetting agents.

The amphiphilic compounds according to this invention are particularly suitable as emulsifiers, demulsifiers, detergents, dispersants and hydrotropes, and antistatics, in industry and domestically, for example in the areas of metal processing, ore production, plastics production and plastics processing, textile auxiliaries, surface treatment, washing and cleaning hard surfaces, especially as manual cleaning agents, washing and cleaning skin and hair, cosmetics, medicine and foodstuff processing and preparation.

In these cases they can be combined with all customary anionic, nonionic, cationic and ampholytic surface-active substances. Examples of nonionic surface-active substances which can be used for a combination and which may be mentioned are fatty acid glycerides, fatty acid polyglycerides, fatty acid esters, ethoxylates of higher alcohols, polyoxyethylene fatty acid glycerides, polyoxyethylen propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkylamines, alkanolamines, alkylamine oxides, derivatives of protein hydrolysates, hydroxy-mixed ethers, alkyl polyglycosides and alkylglucamides.

Examples of anionic surface-active substances which can be used for combinations and which may be mentioned are soaps, ether carboxylic acids and salts thereof, alkylsulphonates, α-olefinsulphonates, α-sulpho fatty acid derivatives, sulphonates of higher fatty acid esters, alcohol sulphates, alcohol ether sulphates, hydroxy-mixed ether sulphates, salts of phosphate esters, taurides, isethionates, linear alkylbenzenesulphonates, alkylarylsulphonates, sulphates of polyoxyethylene fatty acid amides and salts of acylamino acids.

Examples of customary cationic surface-active substances which can be used for combinations and which may be mentioned are alkyltrimethylammonium salts, dialkyldimethylammonium salts, alkyldimethylbenzylammonium salts, alkylpyridinium salts, alkylisoquinolinium salts, benzethonium chlorides and cationic acylamino acid derivatives.

Examples of ampholytic surface-active substances which can be used for combinations and which may be mentioned are amino acids, betaines, sulphobetaines, imidazoline derivatives, soya oil lipids and lecithin.

Furthermore, the amphiphilic compounds according to the invention can also be combined together on their own.

It is likewise possible to add conventional additives to the amphiphilic compounds according to the invention. Such additives are specifically selected for a formulation and comprise, for example, inorganic salts such as sodium chloride and sulphate, and builders, hydrotropes, UV absorbers, softening agents, chelating agents, viscosity modifiers and fragrances.

The abovementioned compounds can be prepared from di-, oligo- or polycarboxylic acids and at least two equivalents of alkoxylated fatty amines and/or alkoxylated fatty acid amides. The anionic amphiphiles can be prepared by reacting the abovementioned products with $SO_3$/inert gas, oleum, chlorosulphonic acid, sulphamic acid, chloroacetic acid salts, isethionates or maleic anhydride and neutralizing with aqueous alkali metal or alkaline earth metal hydroxides or aqueous ammonia or alkanolamines. If required, the products are bleached in aqueous solution with hydrogen peroxide (0.1 to 2.0% based on solid).

We claim:

1. Amphiphilic ester compounds of the general formula I

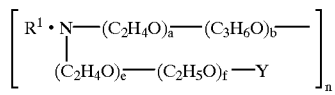

-continued

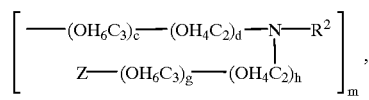

in which $R^1$ and $R^2$ are, independently of one another, a hydrocarbon radical with 1 to 22 carbon atoms or an acyl radical with 2 to 23 carbon atoms, A is a di-, oligo- or polycarbonyl moiety, Y and Z are, independently of one another, hydrogen or the functional group —$CH_2COOM$, —$SO_3M$, —$C_2H_4SO_3M$, —$C(O)C_2H_3(SO_3M)COOM'$ or —$P(O)(OM)_2$ where M, M'=alkali metal, ammonium, alkanolammonium or ½ alkaline earth metal, where at least Y or Z is different from hydrogen, n and m are each, independently of one another, at least 1, and a, b, c, d, e, f, g and h are, independently of one another, numbers from 0 to 15, where the total of a and b, c and d, e and f, and g and h must, in each case, be at least 1, and where the alkoxide units are incorporated randomly or blockwise in any desired sequence.

2. Amphiphilic compounds according to claim 1, characterized in that A is a spacer which consists of a straight-chain or branched, saturated or unsaturated, acyclic or cyclic, aliphatic or aromatic di-, oligo- or polycarbonyl moiety.

3. Amphiphilic compounds according to claim 1, characterized in that the hydrocarbon radicals or acyl radicals $R^1$ and $R^2$ are unbranched or branched, saturated or unsaturated.

4. Amphiphilic compounds according to claim 1, characterized in that $R^1$ and $R^2$ are, independently of one another, a hydrocarbon radical with 6 to 18 carbon atoms or an acyl radical with 7 to 19 carbon atoms.

5. A method of cleaning and washing textiles, comprising contacting the textiles with the amphiphilic compounds according to claim 1.

6. A method of cleaning hard surfaces, comprising contacting the hard surfaces with the amphilic compounds according to claim 1.

7. A method of cleaning and washing skin and hair, comprising contacting the skin and hair with the amphiphilic compounds according to claim 1.

8. A method of emulsifying or demulsifying a composition, comprising adding the amphiphilic compounds according to claim 1, to the composition.

9. A process for producing the amphiphilic ester compounds according to claim 1, comprising:

forming an ester from (i) a di-, oligo- or polycarboxylic acid, and (ii) at least two equivalents of at least one member selected from the group consisting of an alkoxylated fatty amine and an alkoxylated fatty acid amides; and optionally further reacting by sulphation, carboxymethylation or conversion into isethionates, taurates or sulphosuccinates.

* * * * *

UNITED STATES PATENT AND TRADEMARK OFFICE
CERTIFICATE OF CORRECTION

PATENT NO. : 5,962,726
DATED : October 5, 1999
INVENTOR(S) : Klaus KWETKAT, et al It is certified that error appears in the above-identified patent and that said Letters Patent is hereby corrected as shown below:

On the title page, item [86] is incorrect, should be:

-- [86]   PCT No.:      PCT/EP96/02242 --

Signed and Sealed this

Sixth Day of June, 2000

*Attest:*

Q. TODD DICKINSON

*Attesting Officer*            *Director of Patents and Trademarks*

UNITED STATES PATENT AND TRADEMARK OFFICE
CERTIFICATE OF CORRECTION

PATENT NO. : 5,962,726

DATED : October 5, 1999

INVENTOR(S): Klaus KWETKAT, et al.

It is certified that an error appears in the above-identified patent and that said Letters Patent is hereby corrected as shown below:

Column 3, claim 1, " 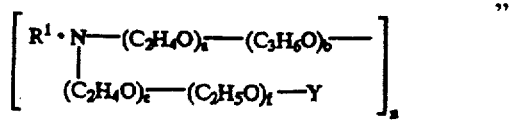 "

should read -- 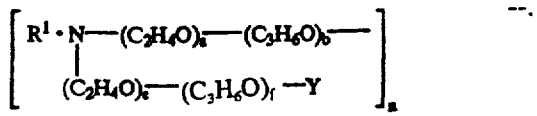 --.

Signed and Sealed this

Fifteenth Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO. : 5,962,726  
DATED : October 5, 1999  
INVENTOR(S) : Klaus Kwetkat, et al Page 1 of 1

It is certified that error appears in the above-identified patent and that said Letters Patent is hereby corrected as shown below:

ABSTRACT,  
Item A, " 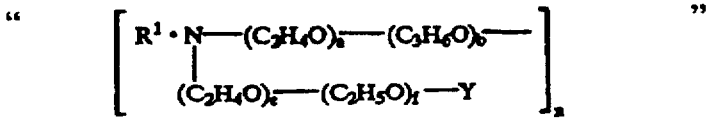 "

should read -- 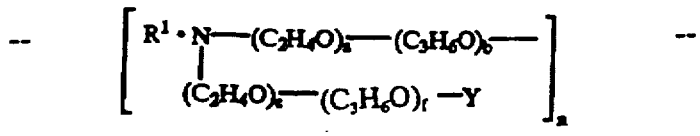 --

Column 2,  
Item A, " 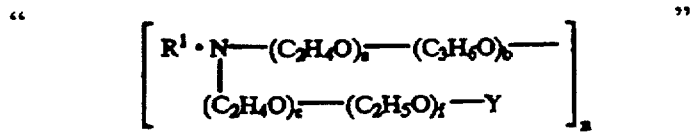 "

should read -- 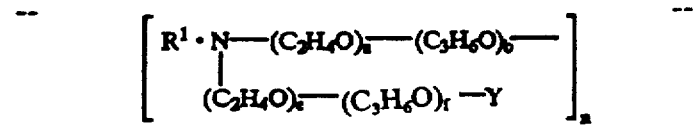 --

Signed and Sealed this

Twenty-seventh Day of November, 2001

Attest:

*Nicholas P. Godici*

NICHOLAS P. GODICI  
*Attesting Officer*   *Acting Director of the United States Patent and Trademark Office*